United States Patent [19]

Thielke et al.

[11] Patent Number: 4,980,368
[45] Date of Patent: Dec. 25, 1990

[54] TRYPTAMINE COMPOUNDS, AND METHODS OF CEREBROVASCULAR TREATMENT THEREWITH

[75] Inventors: Dietrich Thielke; Dagmar Hoeltje, both of Gronau, Fed. Rep. of Germany

[73] Assignee: Beecham-Wuelfing GmbH & Co. KG, Fed. Rep. of Germany

[21] Appl. No.: 946,387

[22] Filed: Dec. 23, 1986

[30] Foreign Application Priority Data

Dec. 23, 1985 [GB] United Kingdom ............... 8531612

[51] Int. Cl.$^5$ ............... C07D 209/16; C07D 209/18; A61K 31/40; A61K 31/395
[52] U.S. Cl. ............... 514/415; 514/212; 514/339; 514/419; 540/524; 546/201; 548/492; 548/504
[58] Field of Search ............... 514/419, 415, 212, 339; 548/492, 504; 540/524; 546/201

[56] References Cited

U.S. PATENT DOCUMENTS

| | | | |
|---|---|---|---|
| 3,042,685 | 7/1962 | Allais et al. | 548/492 |
| 3,217,029 | 11/1965 | Shavel et al. | 548/492 |
| 3,296,072 | 1/1967 | Szmuszkovicz | 514/415 |
| 3,639,414 | 2/1972 | Archer | 548/492 |
| 3,910,953 | 10/1975 | Szantay et al. | 548/492 |

FOREIGN PATENT DOCUMENTS

| | | | |
|---|---|---|---|
| 613852 | 1/1961 | Canada | 548/504 |
| 841524 | 7/1960 | United Kingdom | 548/492 |
| 859223 | 1/1961 | United Kingdom | 548/504 |
| 888426 | 1/1962 | United Kingdom | 548/492 |

Primary Examiner—David B. Springer
Attorney, Agent, or Firm—Jacobs & Jacobs

[57] ABSTRACT

A compound of formula (I) or a pharmaceutically acceptable salt thereof:

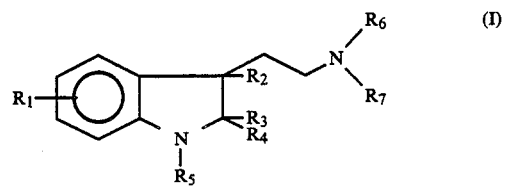

wherein:
$R_1$ is hydrogen, $C_{1-6}$ alkyl, $C_{1-6}$ alkoxy or halogen;
$R_2$ and $R_3$ are both hydrogen or together represent a bond;
$R_4$ is selected from $C_{1-6}$ alkyl, phenyl, phenyl $C_{1-4}$ alkyl, $COR_8$ where $R_8$ is hydroxy, $C_{1-6}$ alkoxy or $NR_9R_{10}$ where $R_9$ and $R_{10}$ are independently hydrogen or $C_{1-4}$ alkyl and $CH_2OR_{11}$ and $R_{11}$ is hydrogen, $C_{1-4}$ alkyl or $C_{1-4}$ alkanoyl;
$R_5$ is hydrogen, $C_{1-6}$ alkyl or phenyl $C_{1-4}$ alkyl;
$R_6$ is phenyl $C_{1-7}$ alkyl in which the phenyl moiety is optionally substituted by one or two of halogen, ortho-nitro, meta- or para-methoxy, methyl or $NR_{12}R_{13}$ wherein $R_{12}$ and $R_{13}$ are independently hydrogen or $C_{1-6}$ alkyl or $R_{12}$ and $R_{13}$ together are $C_{2-6}$ polymethylene or the phenyl moiety is 3,4-disubstituted by methylenedioxy or ethylenedioxy; and
$R_7$ is hydrogen or $C_{1-4}$ alkyl, processes for its preparation and its use as a pharmaceutical.

39 Claims, No Drawings

TRYPTAMINE COMPOUNDS, AND METHODS OF CEREBROVASCULAR TREATMENT THEREWITH

This invention relates to compounds having pharmacological activity, to a process for their preparation and their use as pharmaceuticals.

Various 3-(2-aminoethyl)indoles are described in the literature. Thus, for example, GB No. 781390 describes the preparation of 3-(2-aminoethyl)indoles by the reduction of a 3-indoleglyoxylylamide of the formula:

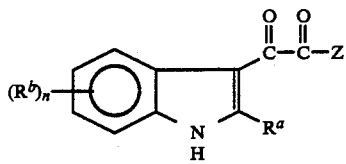

wherein $R^a$ is hydrogen, or an aryl, substituted aryl, aralkyl, or substituted aralkyl radical, preferably containing not more than fifteen carbon atoms, or an alkyl radical of not more than eight carbon atoms, $R^b$ is hydrogen or a halogen atom, or a cyano, carboxy, carbalkoxy (wherein the alkyl group contains 1-8 carbon atoms), dialkylamino or alkyl or alkoxy group (containing 1-8 carbon atoms), or a substituted or unsubstituted aryl, aralkyl, aryloxy, benzyloxy or benzhydryloxy group, an acyloxy (wherein the acyl group is from an organic carboxylic acid containing from 1-8 carbon atoms) or a fused arylene radical, $R^b$ being preferably a group of not more than fifteen carbon atoms, n is zero or an integer from one to four, and Z is a primary secondary or tertiary amido radical suitably derived from ammonia, a primary or secondary alkyl, cycloalkyl, aralkyl or aryl amine or a heterocyclic amine such as piperidine, morpholine, thiamorpholine, pyrrolidine, hexamethyleneimine, tetrahydroisoquinoline or hexahydroisoquinoline.

Examples of 3-(2-aminoethyl)indoles prepared by this route include 7-methoxy-2-benzyl-3-(2-N-benzylaminoethyl)indole and 2-hexyl-3-(2-N-phenethylamino-ethyl)indole.

A novel group of compounds has now been discovered to have anti-hypoxic activity and/or activity against cerebral oxygen deficiency.

Accordingly, the present invention provides a compound of formula (I) or a pharmaceutically acceptable salt thereof:

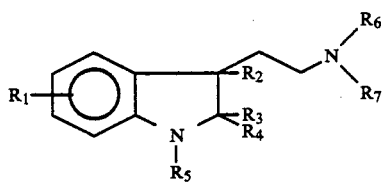

wherein:

$R_1$ is hydrogen, $C_{1-6}$ alkyl, $C_{1-6}$ alkoxy or halogen;

$R_2$ and $R_3$ are both hydrogen or together represents a bond;

$R_4$ is selected from $C_{1-6}$ alkyl, phenyl, phenyl $C_{1-4}$ alkyl, $COR_8$ where $R_8$ is hydroxy, $C_{1-6}$ alkoxy or $NR_9R_{10}$ where $R_9$ and $R_{10}$ are independently hydrogen or $C_{1-4}$ alkyl and $CH_2OR_{11}$ where $R_{11}$ is hydrogen, $C_{1-4}$ alkyl or $C_{1-4}$ alkanoyl;

$R_5$ is hydrogen, $C_{1-6}$ alkyl or phenyl $C_{1-4}$ alkyl;

$R_6$ is phenyl $C_{1-7}$ alkyl in which the phenyl moiety is optionally substituted by one or two of halogen, ortho-nitro, meta-or para-methoxy, methyl or $NR_{12}R_{13}$ wherein $R_{12}$ and $R_{13}$ are independently hydrogen or $C_{1-6}$ alkyl or $R_{12}$ and $R_{13}$ together are $C_{2-6}$ polymethylene or the phenyl moiety is 3,4-disubstituted by methylenedioxy or ethylenedioxy; and $R_7$ is hydrogen or $C_{1-4}$ alkyl.

The compounds of the present invention have anti-hypoxic activity and/or activity against cerebral oxygen deficiency and are therefore useful in treating cerebrovascular disorders and disorders associated with cerebral senility.

Suitable examples of $R_1$ include hydrogen, methyl, ethyl, n- and iso - propyl, n-, sec-,iso- and tert-butyl, methoxy, ethoxy, fluoro and chloro. $R_1$ is preferably hydrogen or methyl, most preferably hydrogen.

$R_2$ and $R_3$ preferably together represent a bond.

$R_4$ is preferably $C_{1-6}$ alkyl or $COR_8$ where $R_8$ is as defined above. Examples of $R_4$ include methyl, ethyl, n and iso-propyl, n, iso, sec and t-butyl, and methoxy carbonyl.

$R_5$ is preferably hydrogen or $C_{1-6}$ alkyl. Examples of $R_5$ include hydrogen, methyl and ethyl.

Examples of $R_6$ include benzyl, phenethyl or 1-methyl-2phenethyl in which the phenyl moiety is optionally substituted by one or two of fluoro, chloro, bromo, amino, methylamino, ethylamino, neo-pentylamino, dimethylamino, diethylamino, di-isopropylamino, 1-piperidyl, 1-pyrrolidyl, ortho-nitro, meta or para-methoxy or methyl, or 3,4-disubstituted by methylenedioxy.

Preferably $R_6$ is benzyl or 1-methyl-2-phenylethyl, optionally monosubstituted in the phenyl moiety by $NR_{12}R_{13}$.

Suitable examples of $R_7$ include hydrogen, methyl, ethyl, n- and iso-propyl, n-, sec-, iso- and tert-butyl.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

There is a favourable group of compounds within formula (I) of formula (II):

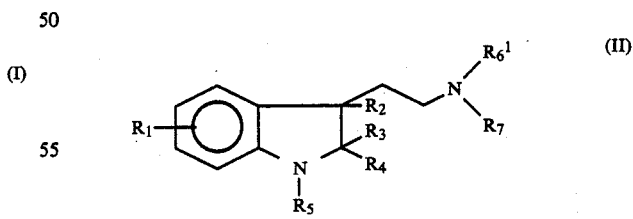

wherein $R_1$, $R_2$, $R_3$, $R_4$, $R_5$ and $R_7$ are as defined in formula (I) and $R_6^1$ is phenyl $C_{1-7}$ alkyl optionally monosubstituted by $NR_{12}R_{13}$ where $R_{12}$ and $R_{13}$ are as defined in formula (I).

Suitable and preferred values for the remaining variables in formula (II) are as described for the corresponding variables under formula (I).

There is a sub-group of compounds within formula (II) of formula (IIa):

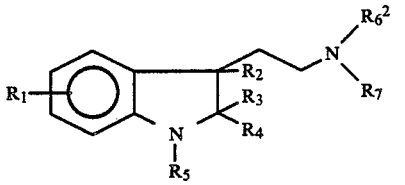

wherein $R_1$, $R_2$, $R_3$, $R_4$, $R_5$ and $R_7$ are as defined in formula (I) and $R_6^2$ is phenyl $C_{1-4}$ alkyl optionally mono-substituted by $NR_{12}R_{13}$ where $R_{12}$ and $R_{13}$ are as defined in formula (II).

Suitable and preferred values for the variables are as described for the corresponding variables under formula (I).

Preferably $R_1$ is hydrogen.
Preferably $R_2$ and $R_3$ represent a bond.
Preferably $R_4$ is methyl or methoxycarbonyl.
Preferably $R_5$ is hydrogen, methyl or ethyl.
Preferably $R_6^2$ is benzyl or 1-methyl-2-phenylethyl optionally meta- or para-substituted by amino optionally substituted by one or two methyl or ethyl groups.
Preferably $R_7$ is hydrogen.

Where compounds of formula (I) can exist in more than one stereoisomeric form, the invention extends to each of these forms and to mixtures thereof.

The invention further provides a process for the preparation of a compound of formula (I), or a pharmaceutically acceptable salt thereof, which process comprises the alkylation of a compound of formula (III):

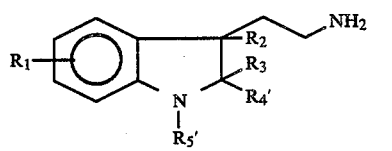

wherein $R_1$, $R_2$ and $R_3$ are as defined in formula (I), $R_4'$ and $R_5'$ are $R_4$ or $R_5$ as defined in formula (I) or groups convertible thereto, to give a compound of formula (IV):

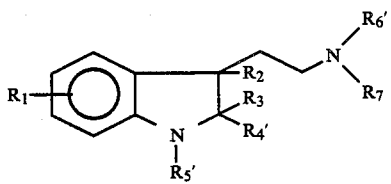

where $R_6'$ is $R_6$ as defined with any amino substituent optionally protected, or containing an amine precursor, and thereafter, optionally and as necessary, de-protecting any protected amino substituent or converting any amine precursor to amine in $R_6'$, converting $R_4'$ and/or $R_5'$ when other than $R_4$ or $R_5$ into $R_4$ and/or $R_5$, interconverting $R_4$, $R_5$, $R_6$ and/or $R_7$ to other $R_4$, $R_5$, $R_6$ or $R_7$, reducing the $R_2/R_3$ bond, and/or forming a pharmaceutically acceptable salt.

Suitable examples of $R_6'$ convertible to $R_6$ include phenyl $C_{1-7}$ alkyl substituted in the phenyl moiety by a protected amino group or an amine precursor.

The alkylation of the compound of formula (III) may be carried out by conventional amine alkylation or, more preferably, by acylation followed by reduction of the amide, or by reductive alkylation.

Acylation may be carried out using the appropriate acyl chloride or anhydride and the subsequent reduction of the resulting amide with $LiAlH_4$, in a suitable inert solvent such as tetrahydrofuran, and optionally in the presence of $AlCl_3$.

The reductive alkylation procedure may be carried out by heating with the aldehyde or ketone in an organic acid, such as acetic acid, then reducing the product in situ using an alkaline borohydride such as sodium borohydride or cyanoborohydride. The reaction can also be carried out in an alcohol, in which case the reduction can be carried out either chemically, for example with a borane such as trimethylammoniumborane or an alkaline borohydride or with hydrogen in the presence of a catalyst such as Raney nickel.

It is also possible to use an aprotic solvent, for example an aromatic solvent such as benzene or toluene, the water formed being eliminated either at room temperature by means of a drying-agent or under reflux heating of the solvent by means of a Dean-Stark water-separator; the reduction can then be expediently carried out with hydrogen in the presence of a catalyst such as palladiated carbon or platinum oxide. These methods may be subject to certain limitations, depending on the nature of the aldehyde or ketone used.

It is also possible to use a more universal method. For example, the compound of formula (III) and the aldehyde or ketone to be condensed are dissolved in a mixture of solvents which can advantageously be a methanol-dichloromethane mixture in the presence of a complex reducing agent such as quaternary ammonium cyanoborohydride or, more simply, an alkaline cyanoborohydride solubilised by a phase-transfer agent, for example sodium cyanoborohydride and aliquat 336(Cf. Hutchins, R. O. and Markowitz, M., Journal of Organic Chemistry 1981, 46, pp.3571–3574).

It will be appreciated that compounds of formula (I) wherein $R_6$ is substituted phenyl $C_{1-7}$ alkyl may be interconverted by conventional procedures including aromatic substituents. Thus, when a phenyl moiety in $R_6'$ is substituted by an amine precursor, conversion of the precursor to amino may be carried out conventionally. For example, when the precursor is nitro, the conversion may be carried out by catalytic reduction, e.g. in the presence of Raney nickel.

When $R_6'$ is an $R_6$ group with a protected amino moiety, the protecting group may be removed conventionally or the protected $R_6$ be converted to the desired $R_6$ group by reduction e.g. with $LiAlH_4$ and $AlCl_3$.

Substitution of the resulting primary amine by $R_{12}$ and $R_{13}$ may be carried out by conventional procedures. Thus conventional amine alkylation, acylation followed by reduction, or reductive alkylation may be employed as described above for the alkylation of the compound of formula (III).

When the acylation/reduction procedure is adopted to give an intermediate where the amine of formula (III) is substituted by phenyl $C_{1-7}$ alkanoyl substituted by alkanoylamino, simultaneous reduction of both alkanoyl moieties may be carried out to give the desired compound of formula (I).

The reduction of the $R_2/R_3$ bond may be carried out conventionally by the use of an alkaline borohydride in a polar aprotic solvent such as dimethylsulphoxide or by nitromethane in the presence of a strong organic acid such as methanesulphonic acid or in pure trifluoroacetic acid. Alternatively the bond may be reduced catalytically with hydrogen over platinum oxide catalyst in a solvent permitting protonation of the indolic nitrogen, such as ethanol containing fluoroboric acid or acetic acid containing trifluoroacetic acid.

Groups $R_5'$ convertible to $R_5$ include conventional amino protecting groups such as $C_{1-6}$ alkoxy carbonyl, aryloxycarbonyl, $C_{1-6}$ alkanoyl or phenyl $C_{1-4}$ alkanoyl, which may be removed by conventional procedures or, where appropriate converted direct to the correspondong $R_5$ group by reduction with $LiAlH_4$ and $AlCl_3$.

Groups $R_4'$ convertible to $R_4$ include the groups mentioned above for $R_5'$ and groups $COR_8'$ where $R_8'$ is protected amino, which can be converted direct to the corresponding group $R_4$ as described above for $R_5$.

Interconversion of $R_4$ and $R_5$ may be performed conventionally, as for example by the conversion of hydrogen to alkyl by conventional alkylation as described for the compound of formula (III), and the interconvertion of groups $R_8$, $R_9$ and $R_{10}$ in $R_5$ by convention esterification/de-esterification and amine alkylation, respectively.

It will be appreciated that these conversions may take place in any desired or necessary order.

Pharmaceutically acceptable salts of the compounds of formula (I) may be formed conventionally by reaction with the appropriate acid such as described above formula (I).

Compounds of formula (III) are known or may be prepared by any of the appropriate methods in conventional indole chemistry. Thus, the aminoethyl moiety may be introduced into the compound of formula (V):

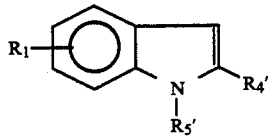

(V)

or the aminoethyl moiety may be incorporated into the indole during the indole synthesis.

Examples of the former method include:
(i) Mannich reaction of the compound of formula (V) with formaldehyde and dimethylamine, followed by treatment with cyanide and reduction of the nitrile by standard methods such as hydrogenation with $PtO_2$ in acetic acid or Raney nickel in alcohol and ammonia; or reduction with $LiAlH_4/AlCl_3$;
(ii) The reaction of the compound of formula (V) with 2-nitroethyl acetate and subsequent reduction of the nitro group by standard methods;
(iii) The conversion of the compound of formula (V) to the indolyl magnesium halide and reaction with α-haloacetonitrile followed by reduction of the nitrile as in (i) above.

Compounds of formula (III) may also be prepared from compounds of formula (V) via a compound of formula (VI):

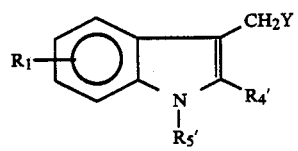

(VI)

where $R_1$, $R_4$, and $R_5'$ are as defined in formula (III) and Y is a conventional amine precursor.

Suitable examples for Y include CN, COQ where Q is H or a leaving group such as halo, $C_{1-4}$ alkoxy or carboxylic acyloxy, and $CH_2L$ where L is $CON_3$, $N_3$, $NO_2$ or X where X is a leaving group such as hydroxy, halo, $C_{1-4}$ alkoxy, $C_{1-4}$ alkanoyloxy, $C_{1-4}$ alkoxycarbonyloxy, tosyloxy or mesyloxy.

The compound of formula (VI) may be prepared conventionally with regard to the group Y. Thus, for example, a compound of formula (VI) may be obtained by reaction of the compound of formula (V) with:

(i) $ClCOCOR_{14}$, where $R_{14}$ is alkoxy such as ethoxy or halo such as chloro, followed by reduction with $LiAlH_4$ to give a compound of formula (VI) where Y is $-CH_2OH$, which may subsequently be reacted with azide ion to give the corresponding compound where Y is $-CH_2N_3$;

(ii) $CH_2=CH-R_{15}$, where $R_{15}$ is a 1-carbonyl containing group or cyano, under basic conditions, followed by hydrolysis and reaction on the resulting acid group by azide ion as described above, to give a compound of formula (VI) where Y is $-CH_2CON_3$;

(iii) formaldehyde in the presence of dimethylamine followed by reaction of cyanide ion on the resulting tertiary amine, if necessary after quaternization, to give a compound of formula (VI) where Y is $-CN$, which may be converted to the compound where Y is $-CHO$ by reaction with diisobutylaluminiumhydride or to the compond where Y is $-COQ$ by hydrolysis of the nitrile under acid conditions to give the corresponding acid, followed by conversion of the hydroxyl group to a leaving group Q such as chloro with a chlorinating agent such as oxalyl chloride;

(iv) $CH_2=CHNO_2$ under basic conditions to give a compound of formula (VI) where Y is $-CH_2NO_2$.

The reaction converting the compound of formula (VI) into that of formula (III) may be carried out under the conventional conditions appropriate to the particular group Y in formula (VI).

Thus, when Y is $CH_2CON_3$, the conversion is a Curtius degradation carried out conventionally, by heating in a dry inert solvent, such as benzene, and then subsequent hydrolysis of the thus formed isocyanate under acid conditions.

When Y is CN, the conversion is a reduction to the primary amine, for example with a reducing agent such as diborane or $LiAlH_4$ at elevated temperature and in an inert solvent such as tetrahydrofuran, or with hydrogen over Raney nickel in the presence of ammonia at ambient temperature in a polar solvent such as methanol.

When Y is CHO, the conversion is a condensation with hydroxylamine followed by reduction of the thus formed oxime over a metallic catalyst, or is a reductive amination with a primary or secondary amine using a reducing agent such as $NaBH_3CN$ in a polar solvent such as $CH_2Cl_2/CH_3OH$ at elevated temperature. Alternatively the intermediate imine may be prepared in a non polar solvent such as benzene in the presence of an acid catalyst e.g. p-toluenesulphonic acid and reduced with a reducing agent such as $NaBH_4$.

When Y is COQ where Q is a leaving group, the conversion is a nucleophilic substitution by ammonia or a primary or secondary amine under conventional conditions appropriate for leaving group Q, followed by reduction of the resulting amide with e.g. $LiAlH_4$ in an inert solvent such as tetrahydrofuran at elevated temperature followed by work up. For example, when Q is halo such as chloro, the nucleophilic substitution may be carried out at ambient or lower temperature in the presence of an acid acceptor such as triethylamine in a polar solvent such as $CH_2Cl_2$, followed by work up to give the amide which may be reduced as just described.

When Y is $CH_2N_3$, the conversion is a reduction of the azide to the primary amine with e.g. hydrogen over a metallic catalyst.

When Y is $CH_2NO_2$, the conversion is a reduction of the nitro group to the primary amine with a reducing agent such as $LiAlH_4$, or hydrogen over Raney nickel or Pd/C catalyst in a polar solvent such as ethanol.

When Y is $CH_2X$, the conversion is a nucleophilic substitution by ammonia or a primary or secondary amine or azide ion, under conventional conditions appropriate for the leaving group X. Thus, when X is hydroxy, it is first converted into a good leaving group such as mesylate or tosylate (using mesyl or tosyl chloride respectively) or chloride (using $SOCl_2$). The nucleophilic substitution may be carried out at elevated temperature in a polar solvent such as acetonitrile in the presence of an acid acceptor such as diisopropyl ethylamine. Alternatively, the leaving group may be substituted by nitrile to yield a compound of formula (VI) where Y=$CH_2CN$. Hydrolysis and conversion by conventional methods yields a compound where Y=$CH_2CON_3$ via the acid by the formation of the acid chloride followed by reaction of azide ion.

Alternatively the aminoethyl moiety may be incorporated during the indole synthesis, for example, by the reaction of phenylhydrazine with:

(a) ethyl-2-oxo-5-phthalimidovalerate to give a compound

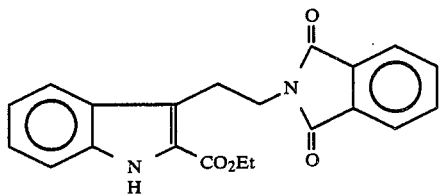

followed by hydrolysis with hydrazine;

(b) diethyl-2-oxo-5-carbethoxamidoadipate to give a compound

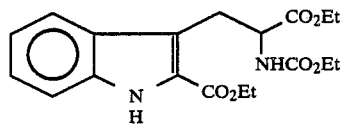

followed by saponification and decarboxylation;

(c) 6,6-Dimethyl-5-oxo-heptanoic acid. The resulting acid may be converted to the amine by the Curtius degradation via the —$CON_3$ compound described above;

(d) keto acids of general formula

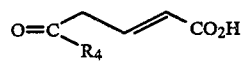

followed by reduction of the double bond and conversion of the acid to the amine as in (c) above.

For further examples of known indole synthesis procedures for the preparation of compounds of formulae (III) and (V), see R. J. Sundberg, "The Chemistry of Indoles", Academic Press, New York, N.Y., 1970, and R. K. Brown in "Indoles," Part 1, W. J. Houlihan, Ed., Wiley-Interscience, New York, N.Y., 1972, and Paul G. Grassmann et al J. Am. Chem. Soc. 96 1974, 5495–5517.

Compounds formula (III) where $R_2$ and $R_3$ are hydrogen may be prepared from the corresponding indole by reduction as described above for the reduction of an $R_2/R_3$ bond in the compound of formula (IV).

In the formulae (V) and (VI) above, the variables are as defined in formula (I) or formula (III).

The invention further provides a process for the preparation of a compound of formula (I), or a pharmaceutically acceptable salt thereof, which process comprises the conversion of a compound formula (VII):

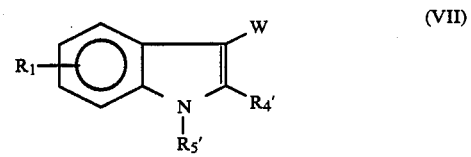

where $R_1$, $R_4'$ and $R_5'$ are as defined in formula (V) and W is a group convertible to $(CH_2)_2NR_6''R_7'$ where $R_6''$ is $R_6$ as defined in formula (I) or a group convertible thereto and $R_7'$ is $R_7$ as defined in formula (I) or an amino protecting group, into a compound of formula (VIIa):

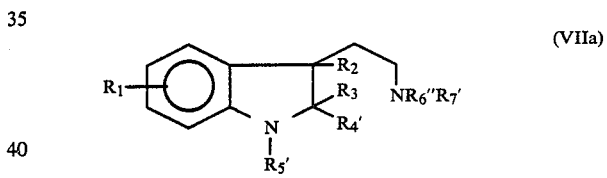

and thereafter, optionally or as necessary converting $R_4'$, $R_5'$, $R_6''$ and/or $R_7'$ when other than $R_4$, $R_5$, $R_6$ or $R_7$ into $R_4$, $R_5$, $R_6$ or $R_7$, interconverting $R_4$, $R_5$, $R_6$ and/or $R_7$ to other $R_4$, $R_5$, $R_6$ or $R_7$, reducing the $R_2/R_3$ bond and/or forming a pharmaceutically acceptable salt.

Examples of $R_6$ convertible to $R_6$ include hydrogen, and $R_6'$ as defined in formula (IV) or phenyl $C_{1-7}$ alkanoyl optionally substituted by a substituent defined for $R_6$ with any amino substituent optionally protected or by an amine precursor.

Examples of W include:
(i) hydrogen, where the conversion reaction is as described above for the preparation of a compound of formula (III) from a compound of formula (V) followed by the alkylation of the compound of formula (III) as described;
(ii) $CH_2Y$ where Y is a conventional amine precursor such as exemplified above, which may be converted to the primary amine of formula (VIIa) where $R_6''$ and $R_7$ are both hydrogen as described for the conversion of the compound of formula (VI) and subsequently alkylated as described for the alkylation of the compound of formula (III). Alternatively, where the conversion employs a primary or secondary amine for reaction with the compound of formula (VII), a compound of formula (VIIa) may be obtained where $R_6''$ is $R_6'$ as previously defined;

(iii) COCOL where L is a leaving group such as halo, which may be converted to the group $(CH_2)_2NR_6''$ by reaction with the appropriate substituted amines followed by reduction with a suitable reducing agent such as lithium aluminium hydride, as generally described in GB No. 781390.

(iv) a group selected form

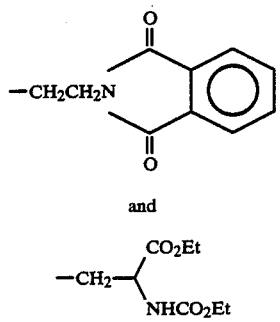

and

—CH$_2$—CH(CO$_2$Et)(NHCO$_2$Et)

which may be converted to the primary amine as described above.

In the case where $R_7'$ is an amino protecting group such as $C_{1-6}$ alkoxycarbonyl, aryloxycarbonyl, $C_{1-6}$ alkanoyl or phenyl $C_{1-7}$ alkanoyl, the protecting group may be removed by conventional procedures. The interconversion of an $R_7$ hydrogen atom may be carried out by conventional amine alkylation as described above for the alkylation of the compound of formula (III).

Conversion of groups $R_4'$ and $R_5'$ in the compound of formula (VIIa), and interconversion of groups $R_1$, $R_2$, $R_3$, $R_4$, $R_5$ and $R_6$ may be carried out as described above for the conversion of the corresponding variables in the compound of formula (IV).

It will be appreciated that the conversions and interconversions of variables in the compound of formula (VIIa) may take place in any desired or necessary order.

The invention further provides a pharmaceutical composition comprising a compound of formula (I) or a pharmaceutically acceptable salt thereof and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10-60% by weight, of the active material, depending on the method of administration.

The invention also provides a method of treatment of cerebrovascular disorders and/or disorders associated with cerebral senility in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg. for example 0.2 to 50 mg; and such unit doses may be administered more than once a day, for example two or three times a day, so that the total daily dosage is in the range of about 0.1 to 100 mg/kg; and such therapy may extend for a number of weeks or months.

At the above indicated dosage range, no toxicological effects are indicated for the compounds of the invention.

In a further aspect the invention provides a compound of formula (I) for use as an active therapeutic substance.

The invention further provides a compound of formula (I) or a pharmaceutically acceptable salt thereof, for use in the treatment of cerebrovascular disorders and/or disorders associated with cerebral senility.

The following examples illustrate the invention and the following descriptions illustrate the preparation of intermediates thereto.

DESCRIPTION 1

1,2-Dimethyl-3-(aminoethyl)indole hydrochloride (D1)

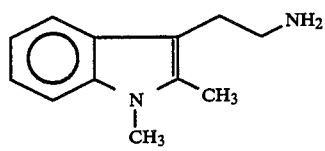

Compound D1 was prepared by conventional procedures from 1,2-dimethylindole.

D1 is described in JP-No. 590 73568-A (Kawaken Fine Chemicals Co. Ltd).

DESCRIPTION 2

2-Methyl-3-(aminoethyl)indole(D2)

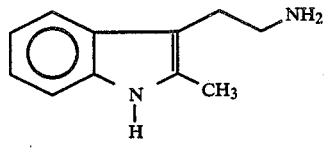

Compound D2 was prepared by conventional procedures from 2-methylindole.

D2 is described by Grandberg, I. I. and Bobrova, N. I. in Khim. Geterotsikl. Soedin. 1974(8)1085.

DESCRIPTION 3

2-Methoxycarbonyl-3-(aminoethyl)indole (D3)

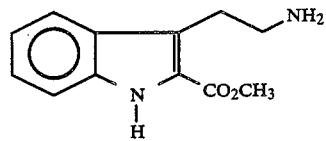

(a) 2-Methoxycarbonylindole 50 g Indole-2-carboxylic acid were stirred with 400 ml methanol/10% $H_2SO_4$ for 48 hours. The resulting crystals were filtered off and washed with methanol giving 51.3 g product.

(b) 3-Dimethylaminomethyl-2-methoxycarbonylindole

To 51 g ester from (a) was added a mixture of 38 ml dimethylamine, 40 ml acetic acid and 23.5 ml formaldehyde (35% in water). After 20 hours stirring at 80° C. the mixture was cooled and the product isolated by acid-base separation.

(c) 2-Methoxycarbonyl-3-cyanomethylindole 40.6 g Product from (b) were dissolved in 300 ml DMSO and 14.5 ml ethylbromide were added. After 10 minutes, 11.4 g KCN were added and the mixture was stirred for 48 hours. The reaction mixture was poured into citric acid and extracted with $CH_2Cl_2$. The solvent was evaporated to give 26 g yellow residue.

(d) Title compound 26 g Product from (c) were dissolved in 1 liter acetic acid, 2 g Pt/C were added and the mixture was hydrogenated at 70 bar for 2 days.

The catalyst was filtered off and the solvent evaporated. Acid-base separation yielded 20.3 g D3 as an oil.

Nmr: ($d_6$-DMSO) δ: 7.85–6.95[4]m; 3.93[3]s; 3.40–2.70[4]m.

EXAMPLE 1

1,2-Dimethyl-3-[2-(1-methyl-2-phenylethyl)aminoethyl]indole hydrochloride (E1)

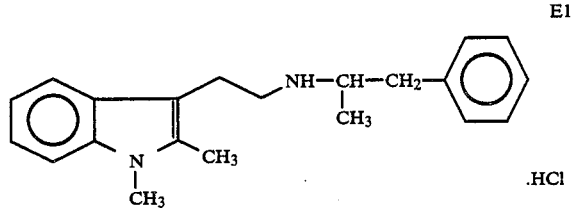

4 g (0.018 moles) D1 were dissolved in 100 ml methanol. Molecular-sieves of 3A were added and the mixture was stirred for ½ hour. Then 2.4 g (0.018 moles) phenylacetone and 1.2 g (0.018 moles)$NaBH_3CN$ were added. After stirring overnight the molecular sieves were filtered off, the solvent was evaporated, and the residue was dissolved in $CH_2Cl_2$, washed with sodium carbonate solution and dried over $Na_2SO_4$. The solvent was evaporated and methanol/HCL was added. The mixture was concentrated and the product crystallised from ethylacetate.

Yield: 2.9g; m.p.: 210° C. Calc. C 73.55 H 7.94 N 8.17 Cl 10.34 found: C 73.68 H 7.89 N 8.42 Cl 10.46

Nmr: ($CDCl_3$/$d_6$-DMSO): δ: 9.9[2]s,broad; 7.63[1]m; 7.15[8]m; 3.58[3]s; 3.30[7]m; 2.35[3]s; 1.41[3]d, J=6.3

EXAMPLE 2

1,2-Dimethyl-3-[2-(4-dimethylaminobenzyl)aminoethyl]indole dihydrochloride, hemihydrate (E2)

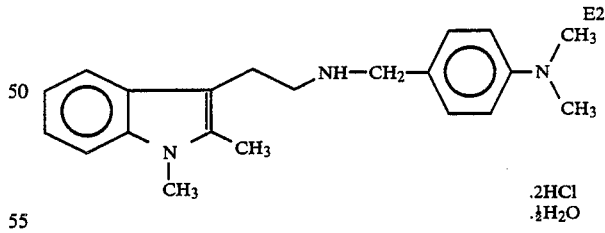

(a) 3.4 g (0.015 moles) D1 were dissolved in 60 ml $CH_2Cl_2$, 10 ml triethylamine and 1.2 equivalents of 4-dimethylaminobenzoic-acid chloride were added with cooling. The mixture was stirred at room temperature for ½ hour and then poured into sodium carbonate solution. The product was extracted with $CH_2Cl_2$, washed with citric acid and dried over $Na_2SO_4$, to give 4.7 g amide 1,2-dimethyl-3-[2-(4-dimethylaminobenzoyl) aminoethyl]indole.

(b) 600 mg (0.015 moles) $LiAlH_4$ were suspended in 40 ml THF. The amide from (a) dissolved in 10 ml THF, was added. The mixture was refluxed for 4 hours.

After cooling, water was added with caution. Aluminium hydroxide was filtered off and washed with THF. The filtrate was concentrated, the residue dissolved in CH$_2$Cl$_2$, washed with water and dried over Na$_2$SO$_4$. The solvent was evaporated and the hydrochloride was formed with HCl/methanol. The product was crystallized from CH$_2$Cl$_2$/isopropanol.

Yield: 2.2 g, m.p.: 192° C. (dec.)

Nmr: (d$_6$-DMSO) δ: 9.65[2]s,broad; 7.35[8]m; 4.12[2]tr; 3.64[3]s; 3.01[10]m; 2.36[3]s;

calc.: C 62.53 H 7.49 N 10.42 Cl 17.58 found: C 62.57 H 7.28 N 10.33 Cl 17.29

EXAMPLE 3

2-Methyl-3-[2-(1-methyl-2-phenylethyl)aminoethyl]indole hydrochloride (E3)

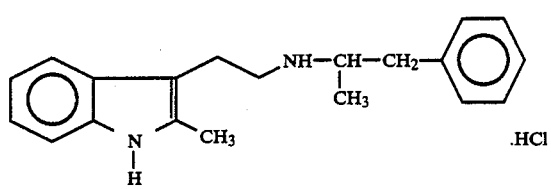

6.79 g (0.032 moles) 2-methyltryptamine were reacted with 4.8 g phenylacetone and 2.3 g NaBH$_3$CN according to Example 1.

The crude product was purified by column-chromatography (CH$_2$Cl$_2$), converted to the hydrochloride with HCl/methanol and crystallized from ethylacetate.

Yield: 3.5g, m.p.; 191° C.

Nmr: (CDCl$_3$/d$_6$ - DMSO) δ: 10.40[1]s; 9.40[2]s, broad; 7.52[1]m; 7.24[6]m; 7.00[2]m; 3.25[7]m; 2.42[3]s; 1.25[3]d, J=6.3 calc.: C 73.04 H 7.66 N 8.25 Cl 10.78 found: C 72.89 H 7.59 N 8.61 Cl 10.61

EXAMPLE 4

2-Methyl-3-[2-(4-dimethylaminobenzyl)aminoethyl]indole dihydrochloride (E4)

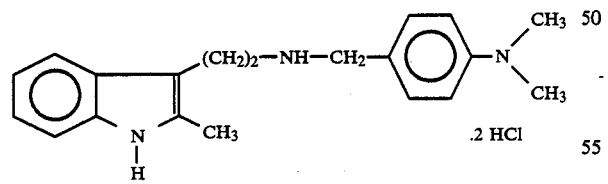

8.5 g (0.049 mol) 2-Methyltryptamine (D2) were reacted with 8.7 g (0.058 mol) 4-dimethylaminobenzaldehyde and 3.1 g (0.05 mol) NaBH$_3$CN according to Example 1.

The crude product was purified by column chromatography (CH$_2$Cl$_2$/5% CH$_3$OH), converted to the hydrochloride with HCl/methanol and crystallised from isopropanol.

NMR: (d6 - DMSO) δ: 10.90 [1]s, broad; 9.60 [2]s, broad; 7.30 [9]m; 4.12 [2]m; 3.02 [10]m; 2.33 [3]s.

EXAMPLE 5

2-Methoxycarbonyl-3-[2-(1-methyl-2-phenylethyl)aminoethyl]indole hydrochloride (E5)

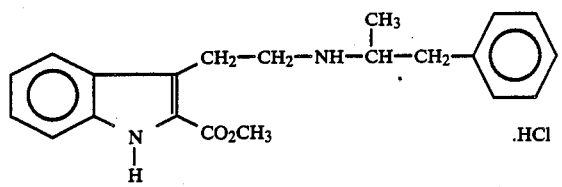

10 g (0.046 mol) 2-Methoxycarbonyl-tryptamine (D3) were reacted with 6.8 g phenylacetone and 3.2 g NaBH$_3$CN according to Example 1.

The product was purified by column chromatography (CH$_2$Cl$_2$/5% CH$_3$OH), converted to the hydrochloride and crystallised from ethylacetate.

Yield: 3.5 g m.p 215° C.

NMR: (d6 - DMSO) δ: 11.76 [1], s; 9.56 [2]s, broad; 7.90 [1]m; 7.30 [8]m; 3.93 [3]s; 3.75–2.60 [7]m; 1.16 [3]d. J=6.4 calc.: C 67.64 H 6.76 N 7.51 Cl 9.51 found: C 66.79 H 6.68 N 7.52 Cl 9.11

EXAMPLE 6

2-Methoxycarbonyl-3-[2-(4-dimethylaminobenzyl)aminoethyl]indole dihydrochloride (E6)

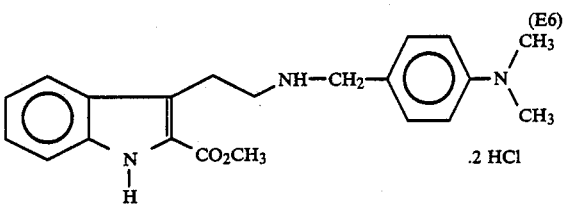

The product was synthesized according to Example 1 from 2-methoxycarbonyltryptamine (D3), 4-dimethylaminobenzaldehyde and NaBH$_3$CN.

m.p.: 215° C.

NMR: d6- DMSO δ: 11.73 [1]s; 9.50 [2]s, broad; 7.40 [9]m; 4.11 [2]m; 3.89 [3]s; 3.50 [2]m; 3.00 [8]m.

calc.: C 59.44 H 6.41 N 9.90 Cl 16.71 found: C 59.56 H 6.46 N 9.87 Cl 16.35

PHARMACOLOGICAL DATA

Triethyltin-induced cerebral oedema in the rat.

The cerebral oedema is induced by oral administrations repeated for 5 consecutive days—one administration per day—of triethyltin chloride at a dose of 2 mg/kg. The study substances are also administered orally twice daily as aqueous solution or suspension at a dose of 1 ml/100 g body-weight; these administrations are given during the 5 days of intoxication with tin. Three groups of 10 male specific pathogen-free (SPF) Wistar rats of 280±10 g body-weight are used for each compound studied:

1 control group 1 group intoxicated with triethyltin 1 group intoxicated with triethyltin and treated with the studied compound.

The rats are killed on the evening of the fifth day; the brain is removed, weighed fresh and after desiccation to constant weight and the water content of each brain is calculated: [H₂O] = fresh weight − dry weight.

The following are then calculated:
the mean water content (M±Sm %) of each group;
the protection index P due to the administered compound:

$$P\% = 1 - \frac{[H_2O] \text{ treated group} - [H_2O] \text{ control group}}{[H_2O] \text{ triethyltin group} - [H_2O] \text{ control group}} \times 100$$

The results are shown in Table 1.

TABLE 1

| Compound | dosage | % reduction | significance |
|---|---|---|---|
| 1 | 12.5 mg/kg | 65 | 0.01 |
| 2 | 50 mg/kg | 100 | 0.01 |
| 3 | 12.5 mg/kg | 42 | 0.01 |

The significance is evaluated by the student t-test.

We claim:

1. A compound of the formula I

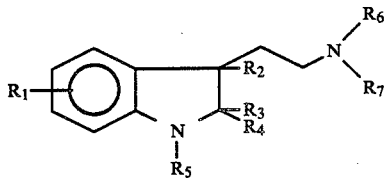

or a pharmaceutically acceptable salt thereof wherein $R_1$ is hydrogen, alkyl of 1–6 carbon atoms, alkoxy of 1–6 carbon atoms or halo; $R_2$ and $R_3$ are both hydrogen or together are a bond; $R_4$ is alkyl of 1–6 carbon atoms, phenyl, phenylalkyl of 1–4 carbon atoms in the alkyl moiety, $COR_8$ wherein $R_8$ is hydroxy, alkoxy of 1–6 carbon atoms or $NR_9R_{10}$ wherein $R_9$ and $R_{10}$ are each hydrogen or alkyl of 1–4 carbon atoms or $CH_2OR_{11}$ wherein $R_{11}$ is hydrogen, alkyl of 1–4 carbon atoms or alkanoyl of 1–4 carbon atoms; $R_5$ is alkyl of 1–6 carbon atoms or phenylalkyl of 1–4 carbon atoms in the alkyl moiety; $R_6$ is phenylalkyl of 1–7 carbon atoms in the alkyl moiety wherein the phenyl moiety is unsubstituted or substituted by 1 or 2 halo, ortho-nitro, meta- or para-methoxy, methyl or $NR_{12}R_{13}$ wherein $R_{12}$ and $R_{13}$ are each hydrogen or alkyl of 1–6 carbon atoms or $R_{12}$ and $R_{13}$ together are polymethylene of 2–6 carbon atoms or the phenyl moiety is 3,4-disubstituted by methylenedioxy or ethylenedioxy; and $R_7$ is hydrogen or alkyl of 1–4 carbon atoms, excluding 7-methoxy-2-benzyl-3-(2-N-benzylaminoethyl)indole and 2-hexyl-3-(2-N-phenethylamino-ethyl)indole.

2. A compound according to claim 1 of the formula II

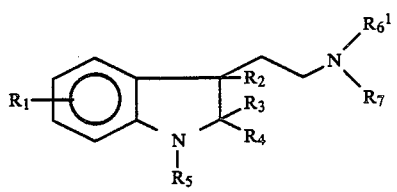

wherein $R_1$ is hydrogen, alkyl of 1–6 carbon atoms, alkoxy of 1–6 carbon atoms or halo; $R_2$ and $R_3$ are both hydrogen or together are a bond; $R_4$ is alkyl of 1–6 carbon atoms, phenyl, phenylalkyl of 1–4 carbon atoms in the alkyl moiety, $COR_8$ wherein $R_8$ is hydroxy, alkoxy of 1–6 carbon atoms or $NR_9R_{10}$ wherein $R_9$ and $R_{10}$ are each hydrogen or alkyl of 1–4 carbon atoms or $CH_2OR_{11}$ wherein $R_{11}$ is hydrogen, alkyl of 1–4 carbon atoms or alkanoyl of 1–4 carbon atoms; $R_5$ is hydrogen, alkyl of 1–6 carbon atoms or phenylalkyl of 1–4 carbon atoms in the alkyl moiety; and $R_7$ is hydrogen or alkyl of 1–4 carbon atoms; $R_6^1$ is phenylalkyl of 1–7 carbon atoms in the alkyl moiety unsubstituted or monosubstituted by $NR_{12}R_{13}$ wherein $R_{12}$ and $R_{13}$ are each hydrogen or alkyl of 1–6 carbon atoms or $R_{12}$ and $R_{13}$ together are polymethylene of 2–6 carbon atoms or the phenyl moiety is 3,4-disubstituted by methylenedioxy or ethylenedioxy.

3. A compound according to claim 1 of the formula IIA

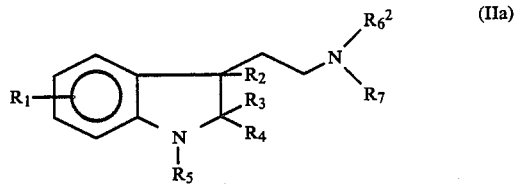

wherein $R_1$ is hydrogen, alkyl of 1–6 carbon atoms, alkoxy of 1–6 carbon atoms or halo; $R_2$ and $R_3$ are both hydrogen or together are a bond; $R_4$ is alkyl of 1–6 carbon atoms, phenyl, phenylalkyl of 1–4 carbon atoms in the alkyl moiety, $COR_8$ wherein $R_8$ is hydroxy, alkoxy of 1–6 carbon atoms or $NR_9R_{10}$ wherein $R_9$ and $R_{10}$ are each hydrogen or alkyl of 1–4 carbon atoms or $CH_2OR_{11}$ wherein $R_{11}$ is hydrogen, alkyl of 1–4 carbon atoms or alkanoyl of 1–4 carbon atoms; $R_5$ is hydrogen, alkyl of 1–6 carbon atoms or phenylalkyl of 1–4 carbon atoms in the alkyl moiety; $R_7$ is hydrogen or alkyl of 1–4 carbon atoms, excluding 7-methoxy-2-benzyl-3-(2-N-benzylamino-ethyl)indole and 2-hexyl-3-(2-N-phenethylamino-ethyl)indole; and $R_6^2$ is phenylalkyl of 1–4 carbon atoms in the alkyl moiety unsubstituted or monosubstituted by $NR_{12}R_{13}$ wherein $R_{12}$ and $R_{13}$ are each hydrogen or alkyl of 1–6 carbon atoms or $R_{12}$ and $R_{13}$ together are polymethylene of 2–6 carbon atoms or the phenyl moiety is 3,4-disubstituted by methylenedioxy or ethylenedioxy.

4. A pharmaceutical composition useful for the treatment of cerebrovascular discorders and disorders associated with cerebral senility in humans and animals, which comprises a therapeutically effective amount of a compound of the formula I

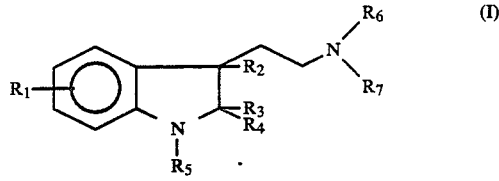

or a pharmaceutically acceptable salt thereof wherein $R_1$ is hydrogen, alkyl of 1–6 carbon atoms, alkoxy of 1–6 carbon atoms or halo; $R_2$ and $R_3$ are both hydrogen or together are a bond; $R_4$ is alkyl of 1–6 carbon atoms, phenyl, phenylalkyl of 1–4 carbon atoms in the alkyl moiety, $COR_8$ wherein $R_8$ is hydroxy, alkoxy of 1–6 carbon atoms or $NR_9R_{10}$ wherein $R_9$ and $R_{10}$ are each hydrogen or alkyl of 1-4 carbon atoms or $CH_2OR_{11}$ wherein $R_{11}$ is hydrogen, alkyl of 1-4 carbon atoms or alkanoyl of 1-4 carbon atoms; $R_5$ is hydrogen, alkyl of 1-6 carbon atoms or phenylalkyl of 1-4 carbon atoms in the alkyl moiety; $R_6$ is phenylalkyl of 1-7 carbon atoms in the alkyl moiety wherein the phenyl moiety is unsubstituted or substituted by 1 or 2 halo, ortho-nitro, meta- or para-methoxy, methyl or $NR_{12}R_{13}$ wherein $R_{12}$ and $R_{13}$ are each hydrogen or alkyl of 1-6 carbon atoms or $R_{12}$ and $R_{13}$ together are polymethylene of 2-6 carbon atoms or the phenyl moiety is 3,4-disubstituted by methylenedioxy or ethylenedioxy; and $R_7$ is hydrogen or alkyl of 1-4 carbon atoms, in combination with a pharmaceutically acceptable carrier.

5. A method of treating cerebrovascular disorders and disorders associated with cerebral senility in humans and animals which comprises administering to a human or animal in need thereof a therapeutically effective amount of a compound of the formula I

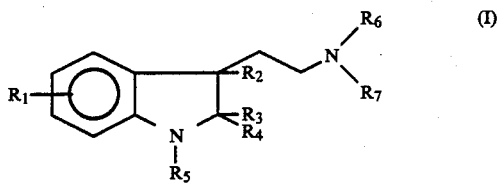

or a pharmaceutically acceptable salt thereof wherein $R_1$ is hydrogen, alkyl of 1-6 carbon atoms, alkoxy of 1-6 carbon atoms or halo; $R_2$ and $R_3$ are both hydrogen or together are a bond; $R_4$ is alkyl of 1-6 carbon atoms, phenyl, phenylalkyl of 1-4 carbon atoms in the alkyl moiety, $COR_8$ wherein $R_8$ is hydroxy, alkoxy of 1-6 carbon atoms or $NR_9R_{10}$ wherein $R_9$ and $R_{10}$ are each hydrogen or alkyl of 1-4 carbon atoms or $CH_2OR_{11}$ wherein $R_{11}$ is hydrogen, alkyl of 1-4 carbon atoms or alkanoyl of 1-4 carbon atoms; $R_5$ is hydrogen, alkyl of 1-6 carbon atoms or phenylalkyl of 1-4 carbon atoms in the alkyl moiety; $R_6$ is phenylalkyl of 1-7 carbon atoms in the alkyl moiety wherein the phenyl moiety is unsubstituted or substituted by 1 or 2 halo, ortho-nitro, meta- or para-methoxy, methyl or $NR_{12}R_{13}$ wherein $R_{12}$ and $R_{13}$ are each hydrogen or alkyl of 1-6 carbon atoms or $R_{12}$ and $R_{13}$ together are polymethylene of 2-6 carbon atoms or the phenyl moiety is 3,4-disubstituted by methylenedioxy or ethylenedioxy; and $R_7$ is hydrogen or alkyl of 1-4 carbon atoms, in combination with a pharmaceutically acceptable carrier.

6. A method according to claim 5 wherein $R_4$ is methyl or methoxycarbonyl.

7. A compound of the formula I

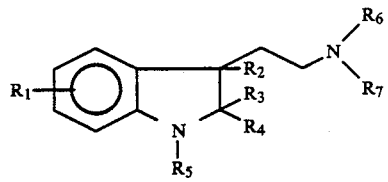

or a pharmaceutically acceptable salt thereof wherein $R_1$ is hydrogen, alkyl of 1-6 carbon atoms, alkoxy of 1-6 carbon atoms or halo; $R_2$ and $R_3$ are both hydrogen or together are a bond; $R_4$ is $COR_8$ wherein $R_8$ is hydroxy, alkoxy of 1-6 carbon atoms or $NR_9R_{10}$ wherein $R_9$ and $R_{10}$ are each hydrogen or alkyl of 1-4 carbon atoms or $CH_2OR_{11}$ wherein $R_{11}$ is hydrogen, alkyl of 1-4 carbon atoms or alkanoyl of 1-4 carbon atoms; $R_5$ is hydrogen, alkyl of 1-6 carbon atoms or phenylalkyl of 1-4 carbon atoms in the alkyl moiety; $R_6$ is phenylalkyl of 1-7 carbon atoms in the alkyl moiety wherein the phenyl moiety is unsubstituted or substituted by 1 or 2 halo, ortho-nitro, meta- or para-methoxy, methyl or by $NR_{12}R_{13}$ wherein $R_{12}$ and $R_{13}$ are each hydrogen or alkyl of 1-6 carbon atoms or $R_{12}$ and $R_{13}$ together are polymethylene of 2-6 carbon atoms or the phenyl moiety is 3,4-disubstituted by methylenedioxy or ethylenedioxy; and $R_7$ is hydrogen or alkyl of 1-4 carbon atoms, excluding 7-methoxy-2-benzyl-3-(2-N-benzylamino-ethyl)indole and 2-hexyl-3-(2-N-phenethylamino-ethyl)indole.

8. A compound according to claim 7 wherein $R_7$ is hydrogen.

9. A compound according to claim 7 wherein $R_1$ is hydrogen.

10. A compound according to claim 7 wherein $R_2$ and $R_3$ are a bond.

11. A compound according to claim 7 wherein $R_4$ is methoxycarbonyl.

12. A compound according to claim 7 wherein $R_5$ is hydrogen, methyl or ethyl.

13. A compound according to claim 7 wherein $R_6$ is benzyl or 1-methyl-2-phenylethyl unsubstituted or substituted at the meta- or para- position by amino which moiety is unsubstituted or substituted by one or two methyl or ethyl moieties.

14. A compound according to claim 7 which is 1,2-dimethyl-3-[2-(1-methyl-2-phenylethyl)aminoethyl]indole; 1,2-dimethyl-3-[2-(4-dimethylaminobenzyl)aminoethyl]indole; 2-methyl-3-[2-(1-methyl-2-phenylethyl)aminoethyl]indole; 2-methyl-3-[2-(4-dimethylaminobenzyl)aminoethyl]indole; 2-methoxycarbonyl-3-[2-(1-methyl-2-phenylethyl)aminoethyl)indole; or 2-methoxycarbonyl-3-[2-(4-dimethylaminobenzyl)aminoethyl)indole or a pharmaceutically acceptable salt thereof.

15. A compound according to claim 7 or a pharmaceutically acceptable salt thereof wherein $R_1$ is hydrogen or alkyl of 1 to 6 carbon atoms; $R_2$ and $R_3$ together are a bond: and $R_5$ is hydrogen or alkyl of 1 to 6 carbon atoms.

16. The compound according to claim 7 which is 2-methoxycarbonyl-3-[(2-(4-dimethylaminobenzyl)aminoethyl]indole or the dihydrochloride salt thereof.

17. A pharmaceutical composition useful for the treatment of cerebrovascular disorders and disorders associated with cerebral senility in humans and animals which comprises a therapeutically effective amount of a compound of the formula I

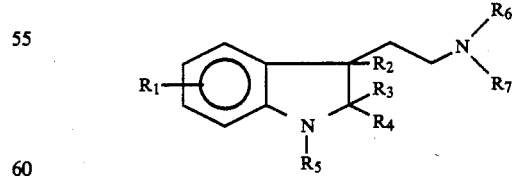

or a pharmaceutically acceptable salt thereof wherein $R_1$ is hydrogen, alkyl of 1-6 carbon atoms, alkoxy of 1-6 carbon atoms or halo; $R_2$ and $R_3$ are both hydrogen or together are a bond; $R_4$ is $COR_8$ wherein $R_8$ is hydroxy, alkoxy of 1-6 carbon atoms or $NR_9R_{10}$ wherein $R_9$ and $R_{10}$ are each hydrogen or alkyl of 1-4 carbon atoms or $CH_2OR_{11}$ wherein $R_{11}$ is hydrogen, alkyl of 1-4 carbon atoms or alkanoyl of 1-4 carbon atoms; $R_5$ is hydrogen, alkyl of 1-6 carbon atoms or phenylalkyl of 1-4 carbon atoms in the alkyl moiety; $R_6$ is phenylalkyl of 1-7 carbon atoms in the alkyl moiety wherein the phenyl moiety is unsubstituted or unsubstituted by 1 or 2 halo, ortho-nitro, meta- or para-methoxy, methyl or by $NR_{12}R_{13}$ wherein $R_{12}$ and $R_{13}$ are each hydrogen or alkyl of 1-6 carbon atoms or $R_{12}$ and $R_{13}$ together are polymethylene of 2-6 carbon atoms or the phenyl moiety is 3,4-disubstituted by methylenedioxy or ethylenedioxy; and $R_7$ is hydrogen or alkyl of 1-4 carbon atoms, excluding 7-methoxy-2-benzyl-3-(2-N-benzylaminoethyl)indole and 2-hexyl-3-(2-N-phenethylamino-ethyl)indole, in combination with a pharmaceutically acceptable carrier.

18. A composition according to claim 17 wherein $R_7$ is hydrogen.

19. A composition according to claim 17 wherein $R_1$ is hydrogen.

20. A composition according to claim 17 wherein $R_2$ and $R_3$ are a bond.

21. A composition according to claim 17 wherein $R_4$ is methyl or methoxycarbonyl.

22. A composition according to claim 17 wherein $R_5$ is hydrogen, methyl or ethyl.

23. A composition according to claim 17 wherein $R_6$ is benzyl or 1-methyl-2-phenylethyl unsubstituted or substituted at the meta- or para position by amino which moiety is unsubstituted or substituted by one or two methyl or ethyl moieties.

24. A composition according to claim 17 wherein the compound is 1,2-dimethyl-3-[2-(1-methyl-2-phenylethyl)aminoethyl]indole; 1,2-dimethyl-3-[2-(4-dimethylaminobenzyl)aminoethyl]indole; 2-methyl-3-[2-(1-methyl-2-phenylethyl)aminoethyl]indole; 2-methyl-3-[2-(4-dimethylaminobenzyl)aminoethyl]indole; 2-methoxycarbonyl-3-[2-(1-methyl-2-phenylethyl)aminoethyl)indole; or 2-methoxycarbonyl-3-[2-(4-dimethylaminobenzyl)aminoethyl)indole or a pharmaceutically acceptable salt thereof.

25. A composition according to claim 17 of the formula II

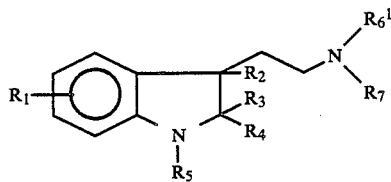

(II)

wherein $R_1$ is hydrogen, alkyl of 1-6 carbon atoms, alkoxy of 1-6 carbon atoms or halo; $R_2$ and $R_3$ are both hydrogen or together are a bond; $R_4$ is $COR_8$ wherein $R_8$ is hydroxy, alkoxy of 1-6 carbon atoms or $NR_9R_{10}$ wherein $R_9$ and $R_{10}$ are each hydrogen or alkyl of 1-4 carbon atoms or $CH_2OR_{11}$ wherein $R_{11}$ is hydrogen, alkyl of 1-4 carbon atoms or alkanoyl of 1-4 carbon atoms; $R_5$ is hydrogen, alkyl of 1-6 carbon atoms or phenylalkyl of 1-4 carbon atoms in the alkyl moiety; and $R_7$ is hydrogen or alkyl of 1-4 carbon atoms; $R_6^1$ is phenylalkyl of 1-7 carbon atoms in the alkyl moiety unsubstituted or monosubstituted by $NR_{12}R_{13}$ wherein $R_{12}$ and $R_{13}$ are each hydrogen or alkyl of 1-6 carbon atoms or $R_{12}$ and $R_{13}$ together are polymethylene of 2-6 carbon atoms or the phenyl moiety is 3,4-disubstituted by methylenedioxy or ethylenedioxy.

26. A composition according to claim 17 of the formula IIA

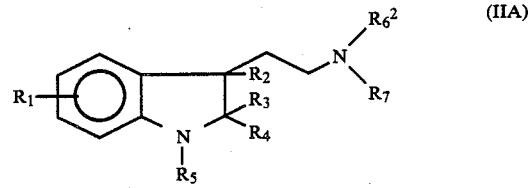

(IIA)

wherein $R_1$ is hydrogen, alkyl of 1-6 carbon atoms, alkoxy of 1-6 carbon atoms or halo; $R_2$ and $R_3$ are both hydrogen or together are a bond; $R_4$ is $COR_8$ wherein $R_8$ is hydroxy, alkoxy of 1-6 carbon atoms or $NR_9R_{10}$ wherein $R_9$ and $R_{10}$ are each hydrogen or alkyl of 1-4 carbon atoms or $CH_2OR_{11}$ wherein $R_{11}$ is hydrogen, alkyl of 1-4 carbon atoms or alkanoyl of 1-4 carbon atoms; $R_5$ is hydrogen, alkyl of 1-6 carbon atoms or phenylalkyl of 1-4 carbon atoms in the alkyl moiety; $R_7$ is hydrogen or alkyl of 1-4 carbon atoms, excluding 7-methoxy-2-benzyl-3-(2-N-benzylamino-ethyl)indole and 2-hexyl-3-(2-N-phenethylamino-ethyl)indole; and $R_6^2$ is phenylalkyl of 1-4 carbon atoms in the alkyl moiety unsubstituted or monosubsubstituted by $NR_{12}R_{13}$ wherein $R_{12}$ and $R_{13}$ are each hydrogen or alkyl of 1-6 carbon atoms or $R_{12}$ and $R_{13}$ together are polymethylene of 2-6 carbon atoms or the phenyl moiety is 3,4-disubstituted by methylenedioxy or ethylenedioxy.

27. A composition according to claim 18 wherein $R_1$ is hydrogen or alkyl of 1 to 6 carbon atoms; $R_2$ and $R_3$ together are a bond; and $R_5$ is hydrogen or alkyl of 1 to 6 carbon atoms.

28. A composition according to claim 17 wherein the compound is 2-methoxycarbonyl-3-[2-(4-dimethylaminobenzyl)aminoethyl]indole or the dihydrochloride salt thereof.

29. A method of treating disorders associated with cerebral senility in humans and animals which comprises administering to a human or animal in need thereof a therapeutically effective amount of a compound of the formula I

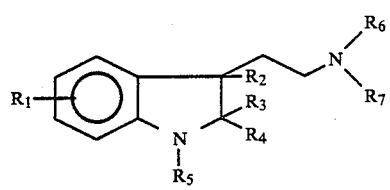

or a pharmaceutically acceptable salt thereof wherein $R_1$ is hydrogen, alkyl of 1-6 carbon atoms, alkoxy of 1-6 carbon atoms or halo; $R_2$ and $R_3$ are both hydrogen or together are a bond; $R_4$ is $COR_8$ wherein $R_8$ is hydroxy, alkoxy of 1-6 carbon atoms or $NR_9R_{10}$ wherein $R_9$ and $R_{10}$ are each hydrogen or alkyl of 1-4 carbon atoms or $CH_2OR_{11}$ wherein $R_{11}$ is hydrogen, alkyl of 1-4 carbon atoms or alkanoyl of 1-4 carbon atoms; $R_5$ is hydrogen, alkyl of 1-6 carbon atoms or phenylalkyl of 1-4 carbon atoms in the alkyl moiety; $R_6$ is phenylalkyl of 1-7 carbon atoms in the alkyl moiety wherein the phenyl moiety is unsubstituted or substituted by 1 or 2 halo, ortho-nitro, meta-or para-methoxy, methyl or by $NR_{12}R_{13}$ wherein $R_{12}$ and $R_{13}$ are each hydrogen or alkyl of 1-6 carbon atoms or $R_{12}$ and $R_{13}$ together are polymethylene of 2-6 carbon atoms or the phenyl moiety is 3,4-disubstituted by methylenedioxy or ethylenedioxy; and $R_7$ is hydrogen or alkyl of 1-4 carbon atoms, excluding 7-methoxy-2-benzyl-3-(2-N-benzylaminoethyl)indole and 2-hexyl-3-(2-N-phenethylamino-ethyl)indole, in combination with a pharmaceutically acceptable carrier.

30. A method according to claim 29 wherein $R_7$ is hydrogen.

31. A method according to claim 29 of the formula II

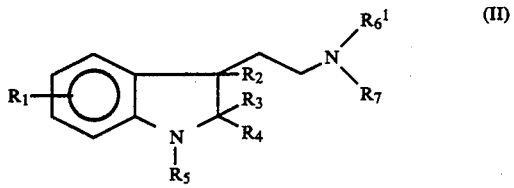

wherein $R_1$ is hydrogen, alkyl of 1-6 carbon atoms, alkoxy of 1-6 carbon atoms or halo; $R_2$ and $R_3$ are both hydrogen or together are a bond; $R_4$ is $COR_8$ wherein $R_8$ is hydroxy, alkoxy of 1-6 carbon atoms or $NR_9R_{10}$ wherein $R_9$ and $R_{10}$ are each hydrogen or alkyl of 1-4 carbon atoms or $CH_2OR_{11}$ wherein $R_{11}$ is hydrogen, alkyl of 1-4 carbon atoms or alkanoyl of 1-4 carbon atoms; $R_5$ is hydrogen, alkyl of 1-6 carbon atoms or phenylalkyl of 1-4 carbon atoms in the alkyl moiety; and $R_7$ is hydrogen or alkyl of 1-4 carbon atoms; $R_6^1$ is phenylalkyl of 1-7 carbon atoms in the alkyl moiety unsubstituted or monosubsubstituted by $NR_{12}R_{13}$ wherein $R_{12}$ and $R_{13}$ are each hydrogen or alkyl of 1-6 carbon atoms or $R_{12}$ and $R_{13}$ together are polymethylene of 2-6 carbon atoms or the phenyl moiety is 3,4-disubstituted by methylenedioxy or ethylenedioxy.

32. A method according to claim 29 of the formula IIA

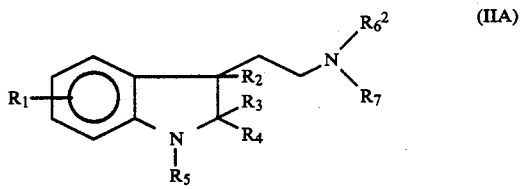

wherein $R_1$ is hydrogen, alkyl of 1-6 carbon atoms, alkoxy of 1-6 carbon atoms or halo; $R_2$ and $R_3$ are both hydrogen or together are a bond; $R_4$ is $COR_8$ wherein $R_8$ is hydroxy, alkoxy of 1-6 carbon atoms or $NR_9R_{10}$ wherein $R_9$ and $R_{10}$ are each hydrogen or alkyl of 1-4 carbon atoms or $CH_2OR_{11}$ wherein $R_{11}$ is hydrogen, alkyl of 1-4 carbon atoms or alkanoyl of 1-4 carbon atoms; $R_5$ is hydrogen, alkyl of 1-6 carbon atoms or phenylalkyl of 1-4 carbon atoms in the alkyl moiety; $R_7$ is hydrogen or alkyl of 1-4 carbon atoms, excluding 7-methoxy-2-benzyl-3-(2-N-benzylamino-ethyl)indole and 2-hexyl-3-(2-N-phenethylamino-ethyl)indole; and $R_6^2$ is phenylalkyl of 1-4 carbon atoms in the alkyl moiety unsubstituted or monosubsubstituted by $NR_{12}R_{13}$ wherein $R_2$ and $R_{13}$ are each hydrogen or alkyl of 1-6 carbon atoms or $R_{12}$ and $R_{13}$ together are polymethylene of 2-6 carbon atoms or the phenyl moiety is 3,4-disubstituted by methylenedioxy or ethylenedioxy.

33. A method according to claim 29 wherein $R_1$ is hydrogen.

34. A method according to claim 29 wherein $R_2$ and $R_3$ are a bond.

35. A method according to claim wherein $R_5$ is hydrogen, methyl or ethyl.

36. A method according to claim 29 wherein $R_6$ is benzyl or 1-methyl-2-phenylethyl unsubstituted or substituted at the meta- or para position by amino which moiety is unsubstituted or substituted by one or two methyl or ethyl moieties.

37. A method according to claim 29 wherein the compound is 1,2-dimethyl-3-[2-(1-methyl-2-phenylethyl)aminoethyl]indole; 1,2-dimethyl-3-[2-(4-dimethylaminobenzyl)aminoethyl]indole; 2-methyl-3-[2-(1-methyl-2-phenylethyl)aminoethyl]indole; 2-methyl-3-[2-(4-dimethylaminobenzyl)aminoethyl]indole; 2-methoxycarbonyl-3-[2-(1-methyl-2-phenylethyl)aminoethyl)indole; or 2-methoxycarbonyl-3-[2-(4-dimethylaminobenzyl)aminoethyl)indole or a pharmaceutically acceptable salt thereof.

38. A method according to claim 29 wherein $R_1$ is hydrogen or alkyl of 1 to 6 carbon atoms; $R_2$ and $R_3$ together are a bond; and $R_5$ is hydrogen or alkyl of 1 to 6 carbon atoms.

39. A method according to claim 29 wherein the compound is 2-methoxycarbonyl-3-[2-(4-dimethylaminobenzyl)aminoethyl]indole or the dihydrochloride salt thereof.

* * * * *